United States Patent
Li et al.

(10) Patent No.: US 11,586,955 B2
(45) Date of Patent: Feb. 21, 2023

(54) ONTOLOGY AND RULE BASED ADJUDICATION

(71) Applicant: ACCENTURE GLOBAL SOLUTIONS LIMITED, Dublin (IE)

(72) Inventors: Chung-Sheng Li, San Jose, CA (US); Guanglei Xiong, Pleasanton, CA (US); Mohammad Ghorbani, Foster City, CA (US); Emmanuel Munguia Tapia, San Jose, CA (US); Sukryool Kang, Sunnyvale, CA (US); Benjamin Nathan Grosof, Mercer Island, WA (US); Ashish Jain, Chennai (IN); Colin Connors, Campbell, CA (US)

(73) Assignee: ACCENTURE GLOBAL SOLUTIONS LIMITED, Dublin (IE)

( * ) Notice: Subject to any disclaimer, the term of this patent is extended or adjusted under 35 U.S.C. 154(b) by 1221 days.

(21) Appl. No.: 16/037,807

(22) Filed: Jul. 17, 2018

(65) Prior Publication Data
US 2019/0244121 A1 Aug. 8, 2019

Related U.S. Application Data

(60) Provisional application No. 62/625,760, filed on Feb. 2, 2018.

(51) Int. Cl.
*G06Q 40/08* (2012.01)
*G06N 5/04* (2006.01)
*G06N 5/046* (2023.01)

(52) U.S. Cl.
CPC ............ *G06N 5/046* (2013.01); *G06Q 40/08* (2013.01)

(58) Field of Classification Search
CPC .................................................... G06Q 40/08
See application file for complete search history.

(56) References Cited

U.S. PATENT DOCUMENTS

| 7,912,705 B2 | 3/2011 | Wasson et al. |
| 9,305,261 B2 | 4/2016 | McClung et al. |
| (Continued) | | |

FOREIGN PATENT DOCUMENTS

| CN | 1361893 A | 7/2002 |
| CN | 101996385 A | 3/2011 |

OTHER PUBLICATIONS

Bin Suo et al., "Computational intelligence approach for uncertainty quantification using evidence theory", Journal of System Engineering and Electronics, vol. 24, No. 2, Apr. 2013, pp. 250-260.
(Continued)

*Primary Examiner* — Maria C Santos-Diaz
(74) *Attorney, Agent, or Firm* — Mannava & Kang, P.C.

(57) ABSTRACT

In an example, an ontology analyzer may generate an ontology, based on a claim adjudication request. The claim adjudication request may be processed, based on the ontology to provide an ontology based inference. A rule based analyzer may identify a predefined rule corresponding to the claim adjudication request and process the request, based on the predefined rule. A conflict resolver may resolve a conflict which may occur between the ontology based inference and the rule based inference. When a conflict is detected, a predefined criteria may be selected for resolving the conflict, the predefined criteria comprising rules to select one of the ontology based inference and the rule based inference to maximize a probability of accurately processing the claim adjudication request in case of a conflict.

15 Claims, 7 Drawing Sheets

(56) References Cited

U.S. PATENT DOCUMENTS

| | | | |
|---|---|---|---|
| 10,552,525 B1* | 2/2020 | Allison | G06Q 10/10 |
| 11,127,082 B1* | 9/2021 | Gore | G06Q 40/08 |
| 2003/0069760 A1 | 4/2003 | Gelber | |
| 2016/0026635 A1 | 1/2016 | Kunapuli et al. | |
| 2017/0017760 A1* | 1/2017 | Freese | G16H 40/63 |
| 2017/0109333 A1* | 4/2017 | Freed | G06F 16/3344 |
| 2019/0006027 A1* | 1/2019 | Sacaleanu | G16H 50/30 |

OTHER PUBLICATIONS

Chen Wei et al., "An Analysis on the Process of Claim With Game Theory", Optimization of Capital Construction, vol. 28, No. 5, Oct. 31, 2007, 3 pages.

* cited by examiner

000# ONTOLOGY AND RULE BASED ADJUDICATION

PRIORITY

The present disclosure claims priority to U.S. Provisional Application 62/625,760 filed on Feb. 2, 2018, the disclosure of which is incorporated by reference herein in its entirety.

BACKGROUND

Claims adjudication refers to a process of paying claims submitted by a person or denying them after comparing the claims with benefits and coverage details indicated in a policy. Claims adjudication process is generally a lengthy and complex process, which involves analysis of data associated with a user and a corresponding policy, based on which a claim is submitted.

The claims adjudication process typically starts with the receiving of a claim request, including details required for processing the claim request. The processing of the claim request for claim adjudication often requires substantial manual intervention. For example, implementation of claims adjudication may require manual development of process maps from policies and generation of rules based on translating natural language content of the policies into rules. Likewise, the data pertaining to users may also need to be processed for analyzing the data with respect to policies. This may entail developing ontologies and inferring from such ontologies. However, curating knowledge in various forms of knowledge representation, such as ontologies and rules, is typically labor intensive and error prone.

Despite the automation of certain processes, considerable manual intervention may be required. For example, in cases where two or independent components for analyzing data in different knowledge forms may provide conflicting results, manual intervention may be required to resolve the conflict. Alternatively, in order to avoid such conflicts a system may be configured to include one of the two components. But this approach may suffer from limitations as well. This is because the system may not benefit from the knowledge obtained by the other component. Indeed, the omitted component may be essential for efficient and accurate claim adjudication and absence of one or more of such components, may affect the claim adjudication process.

Consequently, such claim adjudication may be labor intensive, costly, time consuming, and error prone or may not be provide for efficient and accurate claim adjudication due to conflicts or absence of certain essential components. There is therefore a need for technical solutions that incorporate different systems for analyzing data in different knowledge forms for more accurate and efficient claims adjudication.

BRIEF DESCRIPTION OF DRAWINGS

Features of the present disclosure are illustrated by way of examples shown in the following figures. In the following figures, like numerals indicate like elements, in which.

DETAILED DESCRIPTION

For simplicity and illustrative purposes, the present disclosure is described by referring mainly to examples thereof. The examples of the present disclosure described herein may be used together in different combinations. In the following description, details are set forth in order to provide an understanding of the present disclosure. It will be readily apparent however, that the present disclosure may be practiced without limitation to all these details. Also, throughout the present disclosure, the terms "a" and "an" are intended to denote at least one of a particular element. As used herein, the term "includes" means includes but not limited to, the term "including" means including but not limited to. The term "based on" means based at least in part on, the term "based upon" means based at least in part upon, and the term "such as" means such as but not limited to.

The present disclosure describes systems and methods for integrating ontology and rule based inferencing for claim adjudication. According to an aspect of the present disclosure, an ontology analyzer and a rule based analyzer function independently to provide support for claim adjudication. On receiving a claim adjudication request, claim data may be extracted. The claim data may include data pertaining to a user and corresponding policy.

The ontology analyzer may analyze received data, such as data associated with a user, to generate ontology and determine the desired logical structure of the received data. For example, the ontology analyzer in case of healthcare related claim adjudication may define the logical structure of the medial diagnosis a patient having a particular medical condition, and the treatment that the patient may undergo. Thus, the ontology analyzer may provide an ontology-based inference, on processing ontology data, such as a knowledge graph, corresponding to the received data. In an example embodiment, an ontology analyzer may use an ontology creation tool such as, for example, web ontology language (OWL), Neo4j, or Protégé to create an ontology-based knowledge graph to provide reasoning or inferencing. The ontology analyzer, in one example, may associate a first confidence score with the ontology-based inference. The confidence score being indicative of a probability of an inference being precise. Thus, the higher the confidence score, the higher is the probability of the inference being precise.

In an example, the confidence score may be derived at the time when the ontology is created automatically or semi-automatically. The confidence score may be based on the statistics in terms of how often a concept occurs in a designated corpus, or based on the observation of how a phenomenon occurs in the real world. For example, the ontology "calcium scoring" "is-a" "cardiac test" has 100% confidence level as this is always true. However, "a person" "has" "diabetes" may have a 9.4% confidence level. This is because; a 2015 study estimated that of the total US population, about 30.3 M have diabetes.

Furthermore, the claim data comprising policy related data may be analyzed by the rule-based analyzer. The policy related data may be processed to generate corresponding production rule(s), interchangeably referred to as rules, for adjudicating a claim request. In other examples, based on the claim data, the rules that may be applicable for the claim adjudication may be identified. The rule-based analyzer may provide a set of rules, which may mathematically delineate a set of finite-length strings over an alphabet.

Accordingly, the claim data may be processed, based on the rules to provide a rule-based inference. In an example, the rule based inference may be that the cost of treatment is valid and within the statutory limits. The rule-based analyzer may also associate a second confidence score with the rule-based inference. In an example embodiment, a production rule system, such as, for example, Drools, may be used to generate rules. In addition, other natural language processing tools may be used to generate the rules. Furthermore, the rules determine an inference by specifying the physical function of how conditions link with actions.

This may be done by performing (1) information extraction of the relevant entities, for example, in case of healthcare claims, information to be extracted may be the procedure code, diagnosis code, service provider name, service date, etc.; (2) classification of the text to determine a condition recited in the text with a confidence score generated by the classification, where a classifier performing the classification may be pre-trained with examples and counter-examples what constitute conditions, what constitute actions, and what could be background explanations (historical data); (3) determining the corresponding action to be taken in case the condition is met; and the rule may also determine an action to be taken if the condition is not met.

Thereafter, a conflict resolver may ascertain if the ontology based inference and the rule-based inference contradict each other. In an example embodiment, a conflict may arise when more than one inferencing rules are activated with potentially conflicting actions. The inferencing rules may be within the same set of rules executed by the rule based analyzer or may belong to different rule based analyzers when the analyzers are federated together. For example, a conflict may be detected, when one action accepts the healthcare claim while the others reject the healthcare claim.

In case it is ascertained that the conflict exists, the conflict resolver may aid in resolving the conflict by generating a final outcome indicative of how to resolve the conflict. The final outcome may include a recommendation on how to resolve the conflict or may be indicative of which of the two inferences is to be selected as the final outcome, based on predefined criteria. The predefined criteria may comprise rules to select one of the ontology based inference and the rule based inference to maximize a probability of accurately processing the claim adjudication request in case of a conflict; The predefined criteria may be, for example, to select the inference with a higher confidence score, to select an inference from an analyzer, which may be given preference in case of a conflict, or to select an inference based on a statistical technique, such as Bayesian technique. One of ordinary skill in the art will appreciate that in case the final inference is selected based on the confidence scores, the confidence score associated with ontology based inference and the rule-based inference contradict may be normalized so that the confidence score can be compared.

Accordingly, based on the predefined criteria, the final outcome may be provided and stored for future use. For example, the outcome of the conflict resolver may be saved in a data store and may be used by the conflict resolver for self learning purposes.

Thus, the present disclosure provides an efficient mechanism for claim adjudication in variety of fields, such as healthcare, finance and accounting, cyber security, or any other domain, where policy based analysis may be required. The present disclosure provides for independent operation of the ontology based analyzer and the rule-based analyzer, where manual intervention is minimized or eliminated. Furthermore, the provision of the conflict resolver provides for generation of inferences based on analysis of various knowledge forms, thereby ensuring accuracy and efficiency of claim adjudication.

Moreover, because the system is capable of analyzing various knowledge forms and resolving conflicts, resources may be better utilized as multiple systems/components need not be implemented. Furthermore, since the errors may be minimized, multiple processing cycles that may be required to rework on the claim adjudication may be saved, thereby further enhancing the efficiency of the system. Therefore, the present disclosure may provide for economic, accurate, and time-effective claim adjudication due to the efficient integration of an ontology based analyzer and rule based analyzer.

Figure 1:
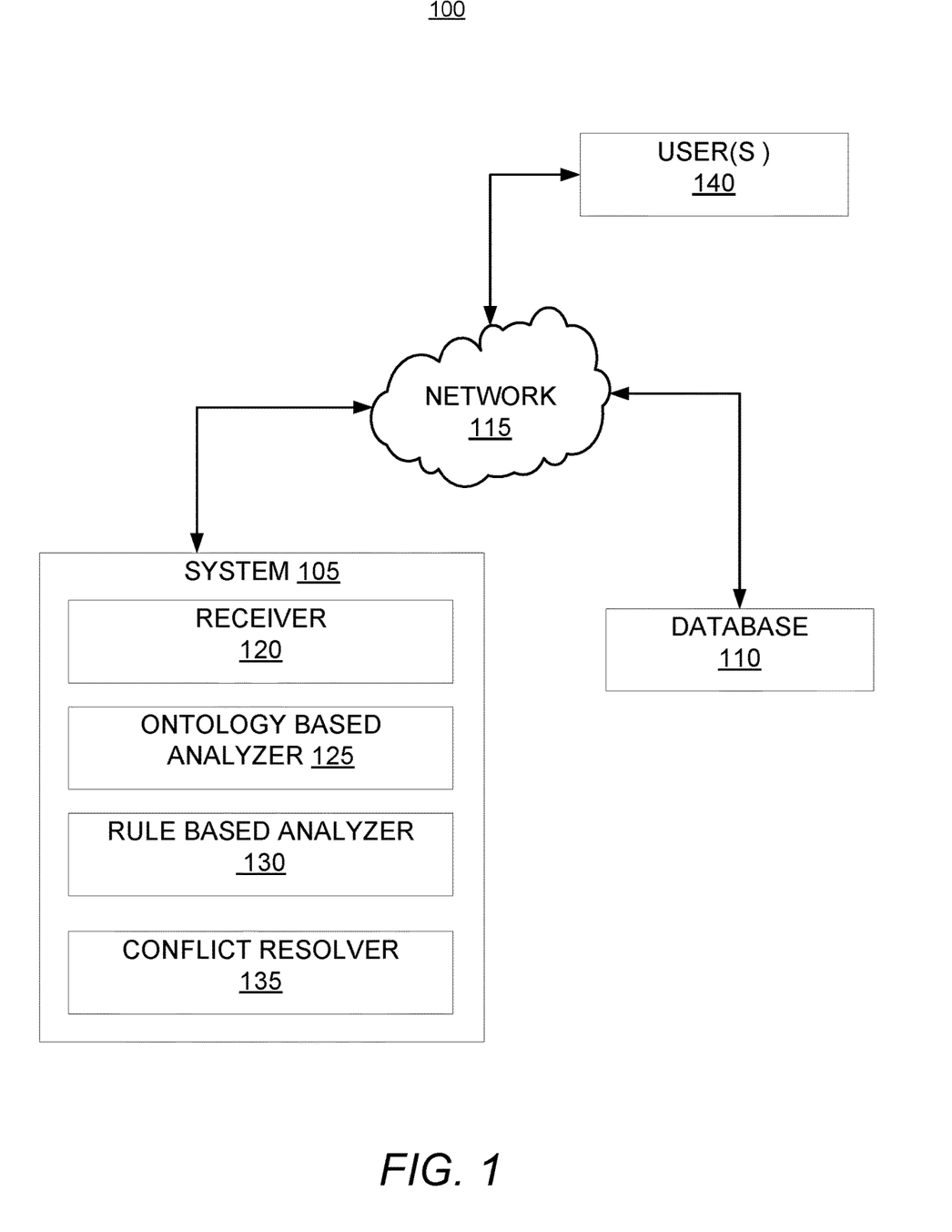
FIG. 1 illustrates an integrated ontology-rule based system in communication with a database, according to an example embodiment of the present disclosure.

FIG. 1 shows a network environment 100 implementing an integrated ontology and rule based inference system 105, as an example of implementation of the present disclosure. The integrated ontology and rule based inference system 105, hereinafter system 105, may provide claim adjudication in a variety of fields including, but not limited to, healthcare, finance and accounting, and cyber security. The description hereinafter is explained with reference to healthcare domain only for the purpose of explanation and should not be construed as limitation.

In an example embodiment, the network environment 100 may be a public network environment, including thousands of individual computers, laptops, various servers, such as blade servers, and other computing devices. In another example embodiment, the network environment 100 may be a private network environment with a limited number of computing devices, such as individual computers, servers, and laptops. Furthermore, the system 105 may be implemented in a variety of computing systems, such as a laptop, a tablet, and the like.

According to an example embodiment, the system 105 is communicatively coupled to with a database 110 through a network 115. In another example, the database 110 may be integrated with the system 105. The database 110 may store data relating to existing policies and their corresponding rules. In an example, the existing policies may be decomposed and curated into multiple knowledge representations, such as frames, data modeling languages, ontologies based knowledge graphs, predicates, and rules. Examples of data modeling languages include Web Ontology Language (OWL) and Resource Description Framework (RDF). The data relating to the existing policies may include any other suitable information related to the existing policies.

In an example, the system 105 may retrieve existing policies from a variety of sources, including third party sources, such as document repositories and other such information sources, data stores, and/or third party applications. The system 105 may further decompose and curate the existing policies into multiple knowledge representations, and store the data into the database 110 for future representation, as is explained in detail later in description of FIG. 1. Further, the database 110 may be accessed whenever policies are to be translated into rules by the system 105. Furthermore, the database 110 may be periodically updated. For example, new data may be added into the database 110, existing data in the database 110 may be modified, or non-useful data may be deleted from the database 110. The database 110 may also include details pertaining to user and associated profiles.

In an example embodiment, the network 115 may be wireless network, a wired network, or a combination thereof. The network 115 may also be an individual network or a collection of many such individual networks, interconnected with each other and functioning as a single large network, e.g., the Internet or an Intranet. The network 115 may be implemented as one of the different types of networks, such as Intranet, Local Area Network (LAN), Wide Area Network (WAN), the Internet, and the like. Further, the network 115 may include a variety of network devices, including routers, bridges, servers, computing devices, storage devices, and the like.

According to an example embodiment, the system 105 may include a receiver 120, an ontology analyzer 125, and a rule based analyzer 130, and a conflict resolver 135. In operation, a claim adjudication request may be received from a user 140 communicating with the system 105. The claim adjudication request may comprise a request for claiming benefits from a policy associated with the user. The claim adjudication request, among other things, may include claim data, which in turn may include one or more of user data and policy data. The user data may include details pertaining to a user, for instance, medical history and current diagnosis, name, age, sex, etc. The policy data may include details pertaining to a policy of the user, such as policy date, terms of the policy, policy ID, etc. The user data and the policy data may be stored in the database 115.

The claim adjudication request may be received by the receiver 120, which may analyze the details of the claims adjudication request. In an example, the claim adjudication request may be made in an optically readable form and the receiver 120 may be an entity, which may be able to read the details of the optical readable claim adjudication request form. The receiver 120 may analyze details such as the policy number, age, user identification, etc., of the user tagging or creating a ticket for the claim adjudication request. The details determined by the receiver 120 are referred to as set of parameters in the present disclosure. In another example, the claim adjudication request may be made on a digital form and the receiver 120 may analyze such digital form to extract required details.

The receiver 120 may then provide the claim data to the ontology analyzer 125 for analyses. The ontology analyzer 125 may analyze the claim data to generate ontology data, such as, for example a knowledge graph representing the claim data. The ontology data may be, for example, in OWL+semantic web rule language (SWRL) language. The ontology data may represent, in an example, the logical structure and relationship between entities in the claim data. The entities may correspond to various features, which may aid in logically structuring the claim data.

Referring to the healthcare domain, the entities may include, for example, age, sex, symptoms, and various tests that may be advised to the user. In an example, the ontology data may determine the relationship between the various medical treatments the user has undergone. The ontology data then be analyzed by the ontology analyzer 125 using ontology based techniques to determine an ontology based inference.

In an example, the ontology based techniques enable the reasoning to, for example, to infer that an entity B has a relationship with an entity A if there is an "is a" edge connecting the entity A to the entity B. In one example, class inference may be used as the ontology based inference. Consider an example, (1) A bus driver is a person that drives a bus. (2) A bus is a vehicle. (3) A bus driver drives a vehicle, so must be a driver. Another type of ontology based inference is instance inference. Consider an example of the reasoning process: (1) Mick drives a white van, (2) Mick must be a person and an adult, so he is a man, (3) Mick is a man who drives a white van, so he's a white van man. (4) A white van man only reads tabloids, and Mick reads the Daily Mirror, thus the Daily Mirror must be a tabloid. Thus, any of such ontology based techniques may be used to determine an ontology based inference.

In an example, the ontology analyzer 125 may capture entities (symbols) used in the production rules for the rule-based analyzer 130. The entities may be defined semi-automatically or fully automatically by the ontology analyzer 125 using representation via a knowledge graph using tools such as RuleML, OWL, RDF, or frame. In other example, the entities may be defined manually. In an example, embodiment, the complete resolution of the definition of entities may occur at run time of "activation" of the rules, thereby allowing delayed, also referred to as "lazy", evaluation of the entities.

The claim adjudication request may be processed, based on the ontology to provide the ontology-based inference. The ontology-based inference may indicate the validity of the details provided in the claim adjudication request.

Furthermore, the ontology analyzer 125 may associate a confidence score with the ontology-based inference. The confidence score may indicate probability of the inference being accurate. Thus, the higher the confidence score, the higher the accuracy of the inference.

In addition to ontology based inference generation, the system 105 provides for rule-based inference generation. For generating rule-based inference for claim adjudication, the rule-based analyzer may analyze claim data, based on predefined rule(s) stored in the database 110. Based on the claim adjudication request, the predefined rules may be identified. Alternatively, the rule based analyzer 130 may generate rules (also referred to as production rules), based on the policy associated with the claim adjudication request submitted by the user 140.

In an example embodiment the rule based analyzer 130 may implement a Drools approach for analyzing claim data. Specifically, in this approach, the rules may be stored in Java code but may also be created separately using Drool Rule Language (DRL). Additionally, the rule based analyzer 130 may use Flexible and customizable (DRL), and Java expressiveness for modeling language expressiveness. Furthermore, the rule-based analyzer 130 may focus on knowledge representation to express propositional and first order logic in a concise, non-ambiguous and declarative manner. Using the techniques described above, the rule based analyzer 130 is able scale to a large number of rules and facts. Furthermore, the rule based analyzer 130 matches' facts and data from the claim data received in the claim adjudication request against rules to infer conclusions.

The rule based analyzer 130 may analyze the claim data with respect to the predefined rules to generate the rule-based inference. The rule-based inference may also aid in determining whether the claim adjudication request is a valid request and accordingly may aid in assessing the compensation to be paid. The rule based analyzer 130 may also associate a confidence score with the rule-based inference.

The system 105 also comprises a conflict resolver 135 which detects if any conflict occurs between the ontology based inference and the rule based inference. In case no conflict is detected, the system 105 may provide a final outcome indicative of a combined ontology based and rule based inference. For example, a report for the claims adjudication may be generated based on the ontology based inference and the rule based inference.

For instance, the ontology based inference may indicate that the healthcare service provider provides psychiatric consultation; and the rule based inference may indicate that the policy established between the payer and healthcare provider stipulates that the psychiatric consultation can only happen at most once a month. Because the ontology based and the rule based inferences are complementary, no conflicts may arise.

Accordingly, based on the combined inference, the claim adjudication may be performed. Referring to previous example, a claim, where the psychiatric consultation is performed only 21 days from the previous consultation may be declined.

If the conflict resolver 135 determines that a conflict has occurred between the ontology based inference and the rule based inference, the conflict resolver 135 resolves the conflict between the ontology based inference and rule based inference to generate the final outcome. The final outcome may include recommendations on how to resolve the conflict. In an example, the conflict resolver 135 resolves the conflict, based on a predefined criteria. The predefined criteria may be, for example, selecting an inference with higher confidence score. In another example, the conflict resolver 135 may implement a statistical technique, such as Bayesian technique to determine an inference. In yet another example, the predefined criteria may indicate that in case of a conflict, inference from a particular analyzer, say, the rule-based analyzer 130 is to be given preference.

Based on the analysis of the conflict resolver 135, the final outcome may be provided. In other examples, the final outcome may include a recommendation for an external agent, who may accordingly further process the request.

The generated outcome may be stored in the database 110. Further, the conflict resolver 135 may also use the generated outcome for self-learning, for example, to handle similar claim adjudication requests in other domains.

Figure 2:
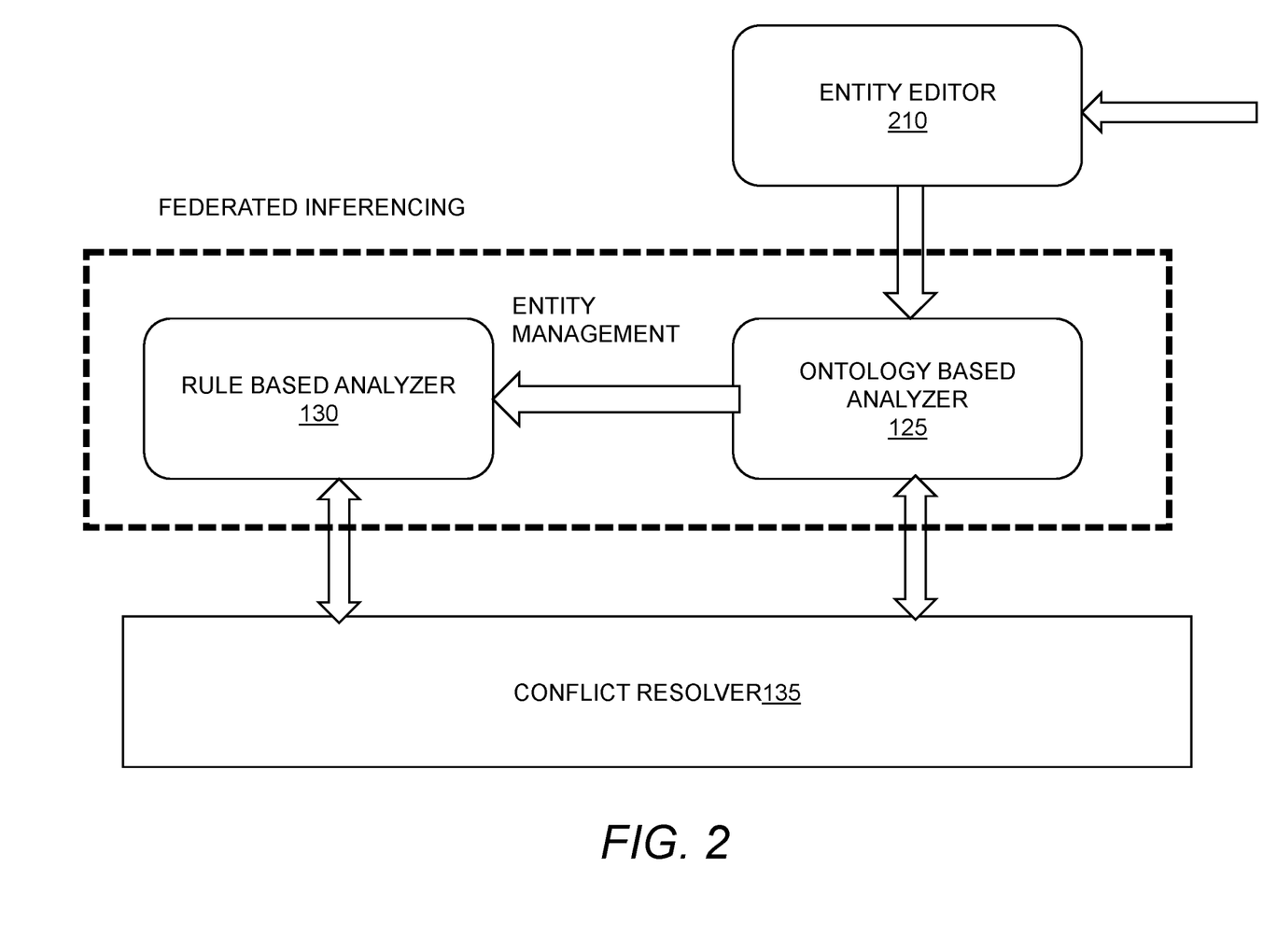
FIG. 2 illustrates a block diagram of the system, according to an example embodiment of the present disclosure.

FIG. 2 schematically illustrates an example process flow 200 with various components of the system 105, according to an example implementation of the present disclosure. In an example, the system 105 may also comprise an entity editor 205 in communication with various other components of the system 105, such as the ontology analyzer 125, the rule based analyzer 130, and the conflict resolver 135. The entity editor 205 may be a separate component or may be integrated with any of the other components, such as the ontology analyzer 125. The entity editor 205 may support in generation or extraction of the entities of a claim adjudication request and may further support to generate ontology based inference. The entity editor 205 may ensure that all of the entities references by the rules are consistent and defined properly. In cases, where a rule base has a number of rules focused on determining the type of entity, it may be beneficial to use the ontology analyzer 125 to perform the initial classification.

As described above, the extracted entities may be used by the ontology analyzer 125 to generate the ontology corresponding to the claim adjudication request and accordingly provide the ontology-based inference. Likewise, the rule-based analyzer 130 may be used to generate the rule-based inference, based on predefined rules, corresponding to the claim adjudication request. The rule based analyzer 130 may implement a set of rules to an input to produce an output. On the other hand the ontology analyzer 125 generates an ontology, which is a description of how things exist according to a particular view. In particular, the ontology may refer to a formal specification of the classes, individuals, attributes, and properties which are relevant to a particular application area.

The conflict resolver 135 may detect whether a conflict exists between the ontology analyzer 125 and the rule based analyzer 130 and resolves the conflicts, based on the predefined criteria discussed in detail above.

Figure 3:
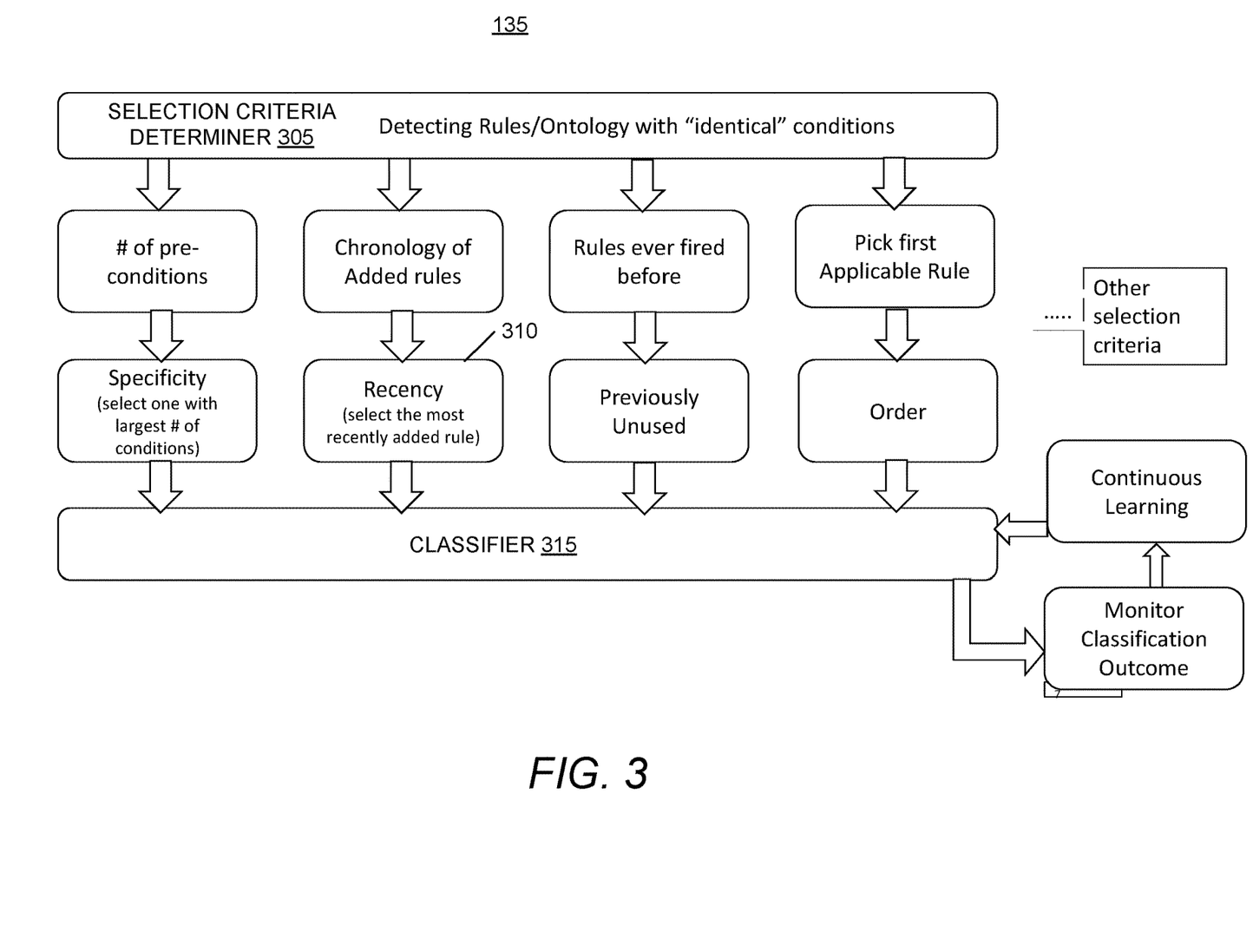
FIG. 3 illustrates an example concept of an integrated ontology and rule based system, according to an example embodiment of the present disclosure.

FIG. 3 illustrates the conflict resolver 135, in an example embodiment of the present disclosure. The conflict resolver 135 comprises a selection criteria determiner 305 that determines the various selection criteria that may be applicable in order to resolve the conflict between the ontology based inference and rule based inference. For instance, the predefined criteria may indicate the rules (production rules or rules used by ontology analyzer) which may have the most specific conditions, will be selected (usually the rules with the largest number of conditions), or the predefined criteria may indicate that the most recent rules are to be applied, or the rules, which have never been used, or the first rule that is encountered in the rule repository, as indicated by 310.

Further, the conflict resolver 135 may include a classifier 315 to classify the various criteria that are applicable on the inferences and generates the final outcome. For example, the classifier 315 may request inputs from an external agent, such as a human agent, to review the decision made by the combination of ontology analyzer 125 and the rule based analyzer 130. The external agent may potentially determine whether the selection rule stipulated was correct or incorrect based on the circumstances. The classifier 315 may be trained on historical data including the data pertaining to external agent's review. In this case, the historical data in terms of how rules have been fired may be used to determine which rule is likely to be selected. Thus, the predefined criteria may gradually approach a most appropriate selection criteria.

Thus, available selection criteria may be provided as input to the classifier 315. Based on the available input and the historical data, the classifier 315 may select one of the selection criteria (predefined criteria) and accordingly action from the rule base analyzer 130 and the ontology analyzer 125 may be obtained.

The conflict resolver 135 may also comprise an outcome monitor (not shown in figures), which may monitor and evaluate the outcome based on a predetermined utility function or by manual audit; and use the results from the utility function or the manual audit to conduct self learning of the conflict resolver 135.

Figure 4:
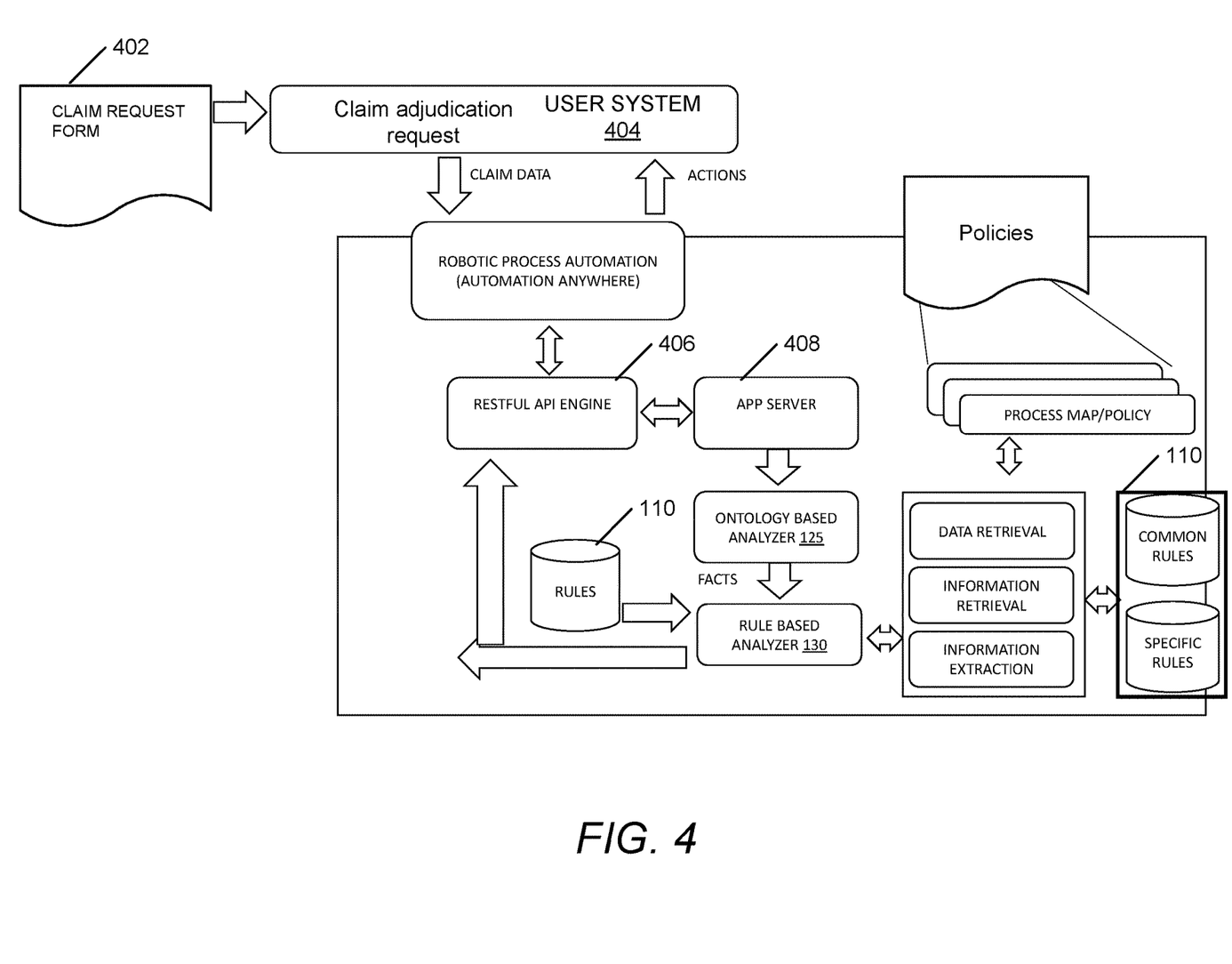
FIG. 4 illustrates a high level schematic of claim adjudication process, according to an example of the present disclosure.

FIG. 4 schematically illustrates an interaction between the various components of the system 105, according to an example implementation of the present disclosure. In general a claim adjudication request by way of a document 402 may be submitted by a user system 404. The document 402 may be digital document or a physical document. From the claim adjudication request, using artificial intelligence (AI) techniques relevant claim data may be extracted. An application programming interface (API) server 406, such as, for example, sprint Boot, and an application server 408, such as, for example, JBOSS, may enable communication between the user device 402 and the components of the system 105. Subsequently, the rule based analyzer 130 and the ontology analyzer 125 may analyze the claim request to generate corresponding inferences.

As discussed above, the ontology-based inference may be generated using ontology analyzing techniques, while the rule based inference may be generated based on corresponding rules. The rule based analyzer 130 may extract rules, common or specific, and may accordingly map the policy corresponding to the claim adjudication request to the predefined rules to generate the rule based inference. The common rules may be applicable to all claim adjudication requests while the specific rules may be applicable to specific claim adjudication requests. The rules may be stored in the database 110. Moreover, the rule based analyzer 130 may periodically update the database 110 with the rules corresponding to various policies.

Further, the conflict resolver 135 analyzes the ontology-based inference and the rule based inference to determine if any conflict occurs between them. If the conflict resolver 135 determines that a conflict exists, the conflict resolver 135 resolves the conflict by any of the methods explained with reference to FIGS. 1-3, to generate the final outcome.

Figure 5:
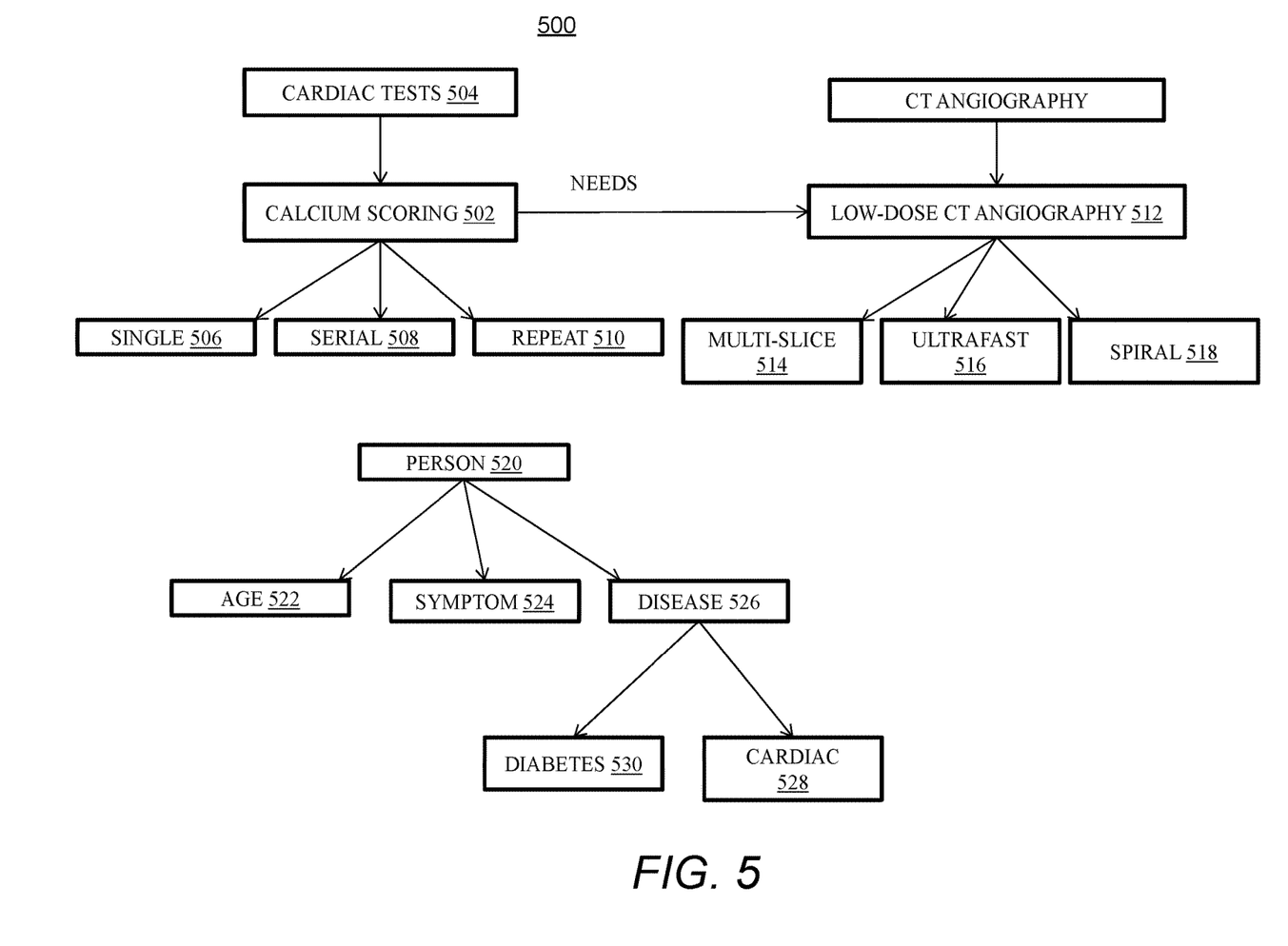
FIG. 5 illustrates an example of an ontology generated by the system, according to an example embodiment of the present disclosure.

FIG. 5 shows an example of an ontology 500 generated by the ontology analyzer 125, according to an example implementation of the present disclosure. The logical structure shows a series of medical diagnosis a cardiac patient can undergo. For example, calcium scoring 502 needs to be done for a person undergoing a cardiac test 504. Further, the logical structure shows the various types of the calcium scoring that can be done. In an example, a single scoring 506, a serial scoring 508, and a repeat scoring 510 may be performed as shown in FIG. 5. Further, the logical structure shows that the person needs to undergo a low-dose computed tomography (CT) angiography 512 after completing the calcium scoring 502. There may be various types of the low-dose CT angiography 512, such as a multi-slice 514, an ultrafast 516, and a spiral 518. The logical structure is saved in the database 110 and the ontology analyzer 125 retrieves the logical structure from the database 110 and thereafter processes the set of parameters to generate an ontology based inference.

Further, to generate the ontology-based inference, a similar logical structure of a person 520 (for whom the claim adjudication request is made) is also created. The logical structure may involve mapping of the age 522, symptom 524, and disease 526 of the person 520. In an example, if the person 520 is determined to be having a cardiac disease 528, the medical diagnosis that he has undergone should match with the logical structure defined for the cardiac disease as this is deemed medically necessary. In another example, if the person 520 is determined to have diabetes, it may be deemed necessary to check whether the medical diagnosis matches the criteria for a patient with diabetes. As a result, the ontological inferencing process is to traverse the ontology by using the entities from the claim as the "fact" to determine whether the claim is consistent with the ontology stored in the database.

Further, the rule based analyzer 130 may analyze the claim data discussed above, based on rules, such as, for example:

a single calcium scoring by means of low-dose multi-slice CT angiography, ultrafast [electron-beam] CT, or spiral [helical] CT medically necessary for screening the following:
 (i) asymptomatic persons age 40 years and older with diabetes; and
 (ii) asymptomatic persons with an intermediate (10% to 20%) 10-year risk of cardiac events based on Framingham Risk Scoring or Pooled Cohort Equations. Serial or repeat calcium scoring is considered experimental and investigational So, accordingly, if the above two conditions (rules) are met, it may be inferred the claim adjudication request is valid and claims may be settled to allow the user to have calcium scoring done.

Figure 6:
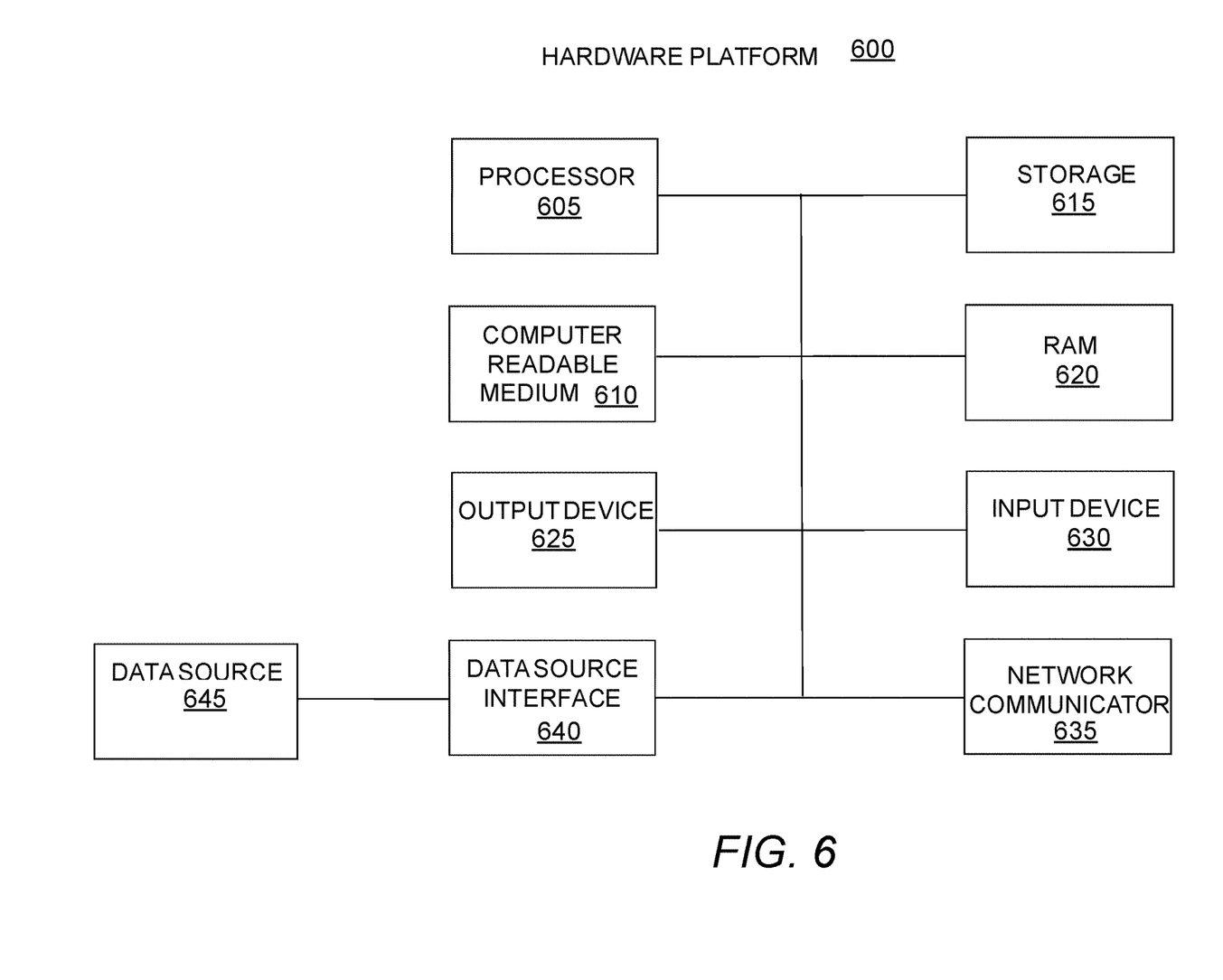
FIG. 6 describes a hardware platform for implementation of the system, according to an example embodiment of the present disclosure.

FIG. 6 illustrates a hardware platform 600 for implementation of the system 105, according to an example of the present disclosure. Particularly, computing machines such as but not limited to internal/external server clusters, quantum computers, desktops, laptops, smartphones, tablets and wearables which may be used to execute the system 105 or may have the structure of the hardware platform 600. The hardware platform 600 may include additional components not shown and that some of the components described may be removed and/or modified. In another example, a computer system with multiple graphical processing units (GPUs) can sit on external-cloud platforms including Amazon Web Services, or internal corporate cloud computing clusters, or organizational computing resources, etc.

Over the FIG. 6, the hardware platform 600 may be a computer system 600 that may be used with the examples described herein. The computer system 600 may represent a computational platform that includes components that may be in a server or another computer system. The computer system 600 may execute, by a processor (e.g., a single or multiple processors) or other hardware processing circuit, the methods, functions and other processes described herein. These methods, functions and other processes may be embodied as machine readable instructions stored on a computer readable medium, which may be non-transitory, such as hardware storage devices (e.g., RAM (random access memory), ROM (read only memory), EPROM (erasable, programmable ROM), EEPROM (electrically erasable, programmable ROM), hard drives, and flash memory). The computer system 600 may include a processor 605 that executes software instructions or code stored on a non-transitory computer readable storage medium 610 to perform methods of the present disclosure. The software code includes, for example, instructions to gather claim data, process claim data, and perform claim adjudication. In an example, the ontology analyzer 125, the rule based analyzer 130, and the conflict resolver 135 are software codes or components performing these steps.

The instructions on the computer readable storage medium 610 are read and stored the instructions in storage 615 or in random access memory (RAM) 620. The storage 615 provides a large space for keeping static data where at least some instructions could be stored for later execution. The stored instructions may be further compiled to generate other representations of the instructions and dynamically stored in the RAM 620. The processor 605 reads instructions from the RAM 620 and performs actions as instructed.

The computer system 600 further includes an output device 625 to provide at least some of the results of the execution as output including, but not limited to, visual information to users, such as external agents. The output device can include a display on computing devices and virtual reality glasses. For example, the display can be a mobile phone screen or a laptop screen. graphical user interfaces (GUIs) and/or text are presented as an output on the display screen. The computer system 600 further includes input device 630 to provide a user or another device with mechanisms for entering data and/or otherwise interact with the computer system 600. The input device may include, for example, a keyboard, a keypad, a mouse, or a touchscreen. In an example, output of the conflict resolver 135 is displayed on the output device 625. Each of these output devices 625 and input devices 630 could be joined by one or more additional peripherals.

A network communicator 635 may be provided to connect the computer system 600 to a network and in turn to other devices connected to the network including other clients, servers, data stores, and interfaces, for instance. A network communicator 635 may include, for example, a network adapter such as a LAN adapter or a wireless adapter. The computer system 600 includes a data source interface 640 to access data source 645. A data source is an information resource. As an example, a database of exceptions and rules may be a data source. Moreover, knowledge repositories and curated data may be other examples of data sources.

Figure 7:
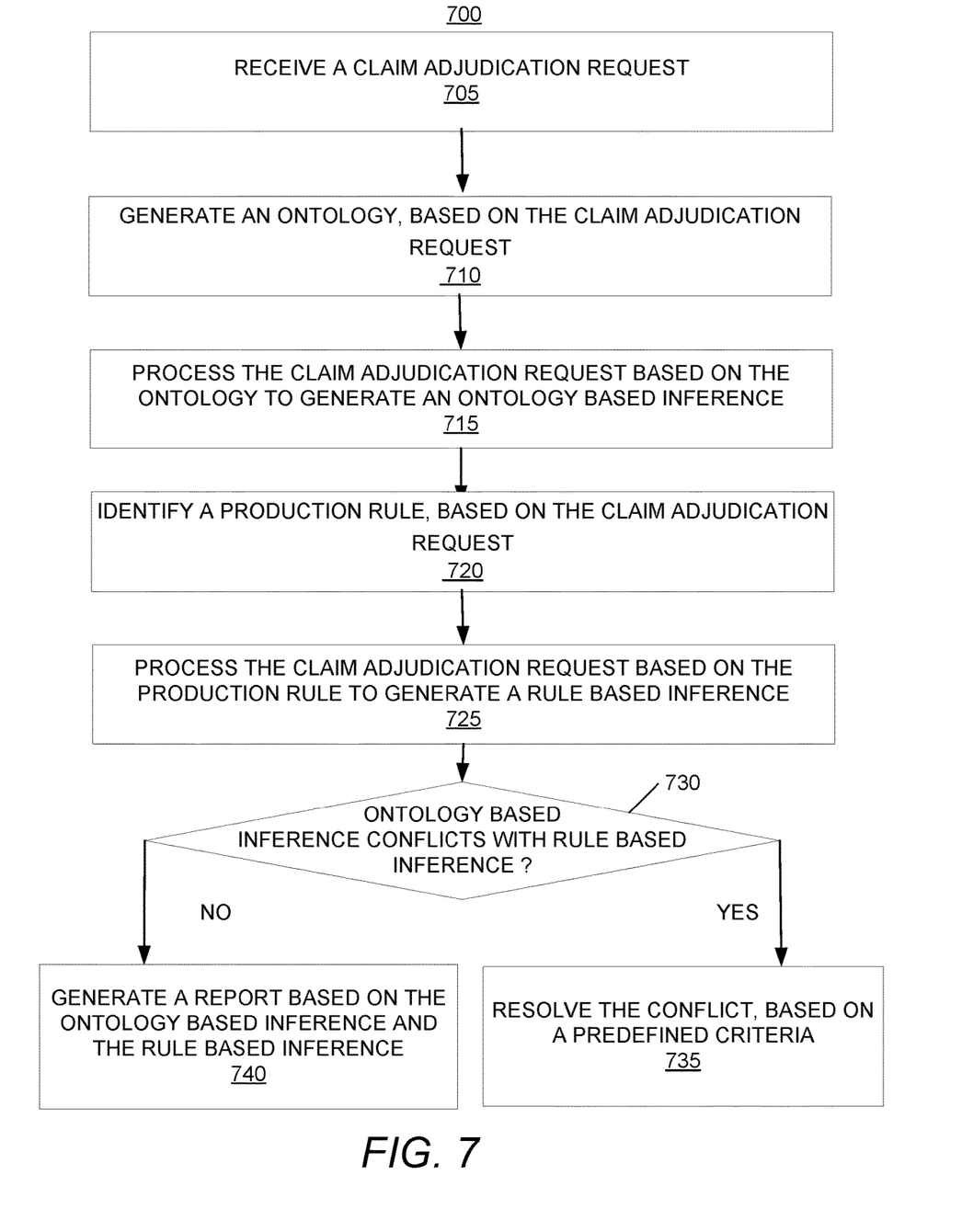
FIG. 7 illustrates a method of claim adjudication with integrated ontology and rule based inferencing, according to an example of the present disclosure.

FIG. 7 shows the method 700 of claim adjudication according to the present disclosure. It should be understood that method steps are shown here for reference only and other combination of the steps may be possible. Further, the method 700 may contain some steps in addition to the steps shown in the FIG. 7. For the sake of brevity, construction and operational features of the system 105 which are explained in detail in the description of FIG. 1, FIG. 2, FIG. 3, FIG. 4, FIG. 5 and FIG. 6 are not explained in detail in the description of FIG. 7.

At block 705, a claim adjudication request is received. The claim adjudication request may be for settling claims pertaining to a variety of domains including, but not limited to, healthcare, finance and accounting, and cyber attack. In an example, the claim adjudication request may be received by the receiver 120. A user may file a claim adjudication request at his service provider digitally or through a paper form. The receiver 120 may extract relevant claim data from the claim adjudication request. The details may include, such as age, gender, policy number, identification, etc., of a user making the claim adjudication request. The extracted claim data may assist in subsequent analysis, such as, assisting in at least one of generating the ontology and identifying the predefined rule.

At block 710, an ontology may be generated, for example, using an ontology generating technique, corresponding to the claim adjudication request. In an example, the ontology analyzer 125 may generate the ontology.

At block 715, the claim adjudication request may be processed, based on the ontology to provide an ontology based inference. In an example, the ontology analyzer 125 may provide ontology based inference. Further, in one example, a first confidence score may be associated with the ontology based inference.

At block 720, a production rule applicable to the claim adjudication request may be identified. The production rule may be predefined or may be generated, while processing the claim adjudication request. The production rule may provide for processing the claim adjudication in a knowledge different from that of the ontology. In an example, the rule based inference may be generated by the rule based analyzer 130.

At block 725, the claim adjudication request may be processed, based on the identified production rule. In an example, the rule based analyzer 130 may process the claim adjudication request. Further, in one example, a second confidence score may be associated with the ontology based inference.

At block 730, it may be ascertained whether the two inferences are conflicting. In an example, the conflict resolver 135 may ascertain whether the inferences are conflicting, for example, it may be determined whether the two inferences contradict each other. If the determination made at block 730 is affirmative, the method proceeds to block 735, where the conflict is resolved to provide a final outcome, based on a predefined criteria. The predefined criteria may include at least one of selecting an inference with a higher confidence score from among the ontology based inference and the rule based inference, implementing a statistical technique to identify a preferred inference from among the ontology based inference and the rule based inference, and selecting an inference from among the ontology based inference and the rule based inference, based on a selection rule indicating the inference to be selected, in case the conflict is detected.

Further, if the determination made at block 730 is negative, the method proceeds to block 740 where a report is generated. The report is indicative of the final outcome based on the ontology based inference and the rule based inference.

What has been described and illustrated herein are examples of the present disclosure along with some of its variations. The terms, descriptions and figures used herein are set forth via illustration only and are not meant as limitations. Many variations are possible within the spirit and scope of the subject matter, which is intended to be defined by the following claims and their equivalents in which all terms are meant in their broadest reasonable sense unless otherwise indicated.

What is claimed is:

1. An integrated ontology and rule based inference system comprising:
    a processor;
    an ontology analyzer coupled to the processor, the ontology analyzer to,
        receive a claim adjudication request from a user device over a network through an application programming interface server, wherein the application programming interface server establishes communication between the integrated ontology and rule based inference system and the user device;
        extract claim data from the claim adjudication request using artificial intelligence (AI) techniques;
        generate an ontology corresponding to a claim adjudication request, using an ontology based technique, wherein the ontology is generated by analyzing the claim data and determining a logical structure of the claim data, and wherein the ontology comprises a knowledge graph representing the claim data; and
        process the claim adjudication request, based on the ontology, to provide an ontology based inference;
    a rule based analyzer coupled to the processor, the rule based analyzer to:
        identify a predefined rule for processing the claim adjudication request; and
        process the claim adjudication request, based on the predefined rule, to provide a rule based inference; and
    a conflict resolver coupled to the processor and in communication with the ontology analyzer and the rule based analyzer, the conflict resolver to,
        ascertain whether the ontology based inference conflicts with the rule based inference, a conflict being detected when the ontology based inference and the rule based inference indicate conflicting actions;
        maximize a probability of accurately processing the claim adjudication request in case the conflict is detected, wherein the probability is maximized by selecting a predefined criteria for resolving the conflict, the predefined criteria comprising rules to select one of the ontology based inference and the rule based inference, wherein the conflict resolver comprises an outcome monitor to evaluate the final outcome based on a predetermined utility function and uses results from the utility function to conduct self-learning of the conflict resolver; and implement the predefined criteria to provide a final outcome indicative of how to resolve the conflict, wherein the predefined criteria is implemented based on the self-learning of the conflict resolver.

2. The integrated ontology and rule based inference system as claimed in claim 1, wherein the ontology analyzer is to associate a first confidence score with the ontology based inference and the rule based analyzer is to associate a second confidence score with the rule based inference.

3. The integrated ontology and rule based inference system as claimed in claim 2, wherein the predefined criteria to select an inference as the final outcome includes at least one of:

selecting the inference with a higher confidence score from among the ontology based inference and the rule based inference;

implementing a statistical technique to identify a preferred inference from among the ontology based inference and the rule based inference; and selecting the inference from among the ontology based inference and the rule based inference, based on a selection rule indicating the inference to be selected, in case the conflict is detected.

4. The integrated ontology and rule based inference system as claimed in claim 1, wherein the claim adjudication request comprises at least one of user data and policy data, the user data comprising details pertaining to a user and the policy data comprising details pertaining to a policy corresponding to the claim adjudication request.

5. The integrated ontology and rule based inference system as claimed in claim 1, wherein the conflict resolver comprises:

a selection criteria determiner to select one or more selection criteria, which are applicable in order to resolve the conflict between the ontology based inference and the rule based inference; and a classifier to select the predefined criteria from the one or more criteria, based on historical data.

6. A method for claim adjudication comprising:

receiving a claim adjudication request from a user device over a network through an application programming interface server, wherein the application programming interface server establishes communication between the integrated ontology and rule based inference system and the user device;

extracting claim data from the claim adjudication request using artificial intelligence (AI) techniques;

generating an ontology corresponding a claim adjudication request, using an ontology based technique, wherein the ontology is generated by analyzing the claim data and determining a logical structure of the claim data, and wherein the ontology comprises a knowledge graph representing the claim data;

processing the claim adjudication request, based on the ontology, to provide an ontology based inference;

identifying a predefined rule for processing the claim adjudication request;

processing the claim adjudication request, based on the predefined rule, to provide a rule based inference;

ascertaining whether the ontology based inference conflicts with the rule based inference, a conflict being detected when the ontology based inference and the rule based inference indicate conflicting actions;

maximizing a probability of accurately processing the claim adjudication request in case the conflict is detected, wherein the probability is maximized by selecting a predefined criteria for resolving the conflict, the predefined criteria comprising rules to select one of the ontology based inference and the rule based inference, wherein the final outcome is evaluated based on a predetermined utility function and results from the utility function are used to conduct self-learning for selecting the predefined criteria; and implementing the predefined criteria to provide a final outcome indicative of how to resolve the conflict, wherein the predefined criteria is implemented based on the self-learning.

7. The method as claimed in claim 6, wherein the method further comprises associating a first confidence score with the ontology based inference and associating a second confidence score with the rule based inference.

8. The method as claimed in claim 7, wherein the predefined criteria to select an inference as the final outcome includes at least one of:

selecting the inference with a higher confidence score from among the ontology based inference and the rule based inference;

implementing a statistical technique to identify a preferred inference from among the ontology based inference and the rule based inference; and selecting the inference from among the ontology based inference and the rule based inference, based on a selection rule indicating the inference to be selected, when the conflict is detected.

9. The method as claimed in claim 6, wherein the claim adjudication request comprises at least one of user data and policy data, the user data comprising details pertaining to a user and the policy data comprising details pertaining to a policy corresponding to the claim adjudication request.

10. The method as claimed in claim 6, wherein selecting the predefined criteria comprises receiving one or more selection criteria, which are applicable in order to resolve the conflict between the ontology based inference and the rule based inference; and selecting the predefined criteria from the one or more criteria, based on historical data.

11. A non-transitory computer readable medium including machine readable instructions that are executable by a processor to:

receive a claim adjudication request from a user device over a network through an application programming interface server, wherein the application programming interface server establishes communication between the integrated ontology and rule based inference system and the user device;

extract claim data from the claim adjudication request using artificial intelligence (AI) techniques;

generate an ontology corresponding a claim adjudication request, using an ontology based technique, wherein the ontology is generated by analyzing the claim data and determining a logical structure of the claim data, and wherein the ontology comprises a knowledge graph representing the claim data;

process the claim adjudication request, based on the ontology, to provide an ontology based inference;

identify a predefined rule for processing the claim adjudication request;

process the claim adjudication request, based on the identified rule, to provide a rule based inference;

ascertain whether the ontology based inference conflicts with the rule based inference, a conflict being detected when the ontology based inference and the rule based inference indicate conflicting actions;

maximize a probability of accurately processing the claim adjudication request in case the conflict is detected, wherein the probability is maximized by selecting a predefined criteria for resolving the conflict, the predefined criteria comprising rules to select one of the ontology based inference and the rule based inference, wherein the final outcome is evaluated based on a predetermined utility function and results from the utility function are used to conduct self-learning for selection of the predefined criteria; and implement the predefined criteria to provide a final outcome indicative of how to resolve the conflict, wherein the predefined criteria is implemented based on the self-learning.

12. The non-transitory computer readable medium as claimed in claim 11, wherein the processor is to associate a first confidence score with the ontology based inference and associating a second confidence score with the rule based inference.

13. The non-transitory computer readable medium as claimed in claim 11, wherein the predefined criteria to select an inference as the final outcome includes at least one of:

selecting the inference with a higher confidence score from among the ontology based inference and the rule based inference;

implementing a statistical technique to identify a preferred inference from among the ontology based inference and the rule based inference; and selecting the inference from among the ontology based inference and the rule based inference, based on a selection rule indicating the inference to be selected, when the conflict is detected.

14. The non-transitory computer readable medium as claimed in claim 11, wherein the claim adjudication request comprises at least one of user data and policy data, the user data comprising details pertaining to a user and the policy data comprising details pertaining to a policy corresponding to the claim adjudication request.

15. The non-transitory computer readable medium as claimed in claim 11, wherein to select the predefined criteria the processor is to:

receive one or more selection criteria, which are applicable in order to resolve the conflict between the ontology based inference and the rule based inference; and select the predefined criteria from the one or more criteria, based on historical data.

* * * * *